(12) United States Patent
Matthews

(10) Patent No.: US 12,186,581 B2
(45) Date of Patent: Jan. 7, 2025

(54) SYSTEM AND METHOD OF TREATING PAIN WITH EXTERNAL TRANS-ZYGOMATIC ARCH PHOTIC STIMULATION

(71) Applicant: Charles Joseph Matthews, Raleigh, NC (US)

(72) Inventor: Charles Joseph Matthews, Raleigh, NC (US)

( * ) Notice: Subject to any disclaimer, the term of this patent is extended or adjusted under 35 U.S.C. 154(b) by 288 days.

(21) Appl. No.: 17/854,491

(22) Filed: Jun. 30, 2022

(65) Prior Publication Data

US 2023/0001230 A1    Jan. 5, 2023

Related U.S. Application Data

(60) Provisional application No. 63/238,843, filed on Aug. 31, 2021, provisional application No. 63/217,481, filed on Jul. 1, 2021.

(51) Int. Cl.
*A61N 5/06*    (2006.01)

(52) U.S. Cl.
CPC .... *A61N 5/0622* (2013.01); *A61N 2005/0651* (2013.01)

(58) Field of Classification Search
CPC .......... A61N 5/0622; A61N 5/06; A61N 5/00; A61N 5/021; A61N 5/024
USPC ........................................................ 607/46
See application file for complete search history.

(56) References Cited

U.S. PATENT DOCUMENTS

2018/0280721 A1* 10/2018 Beckner ............... A61B 5/0532

* cited by examiner

*Primary Examiner* — Nadia A Mahmood
(74) *Attorney, Agent, or Firm* — Ashley D. Johnson; Dogwood Patent and Trademark Law

(57) ABSTRACT

The invention is method comprising the use of an external photic stimulator treat and/or prevent pain in a subject, such as migraine headache, dental pain, and/or other sources of cranial pain. The presently disclosed method includes treating the pain externally through the cheek, over the zygomatic arch and area of the trigeminal ganglion. The external photic stimulation is believed to inhibit excessive firing of trigeminal ganglion circuits, preventing the excessive expression of calcitonin gene-related peptides and/or other inflammatory manifestations of the pain.

18 Claims, 7 Drawing Sheets

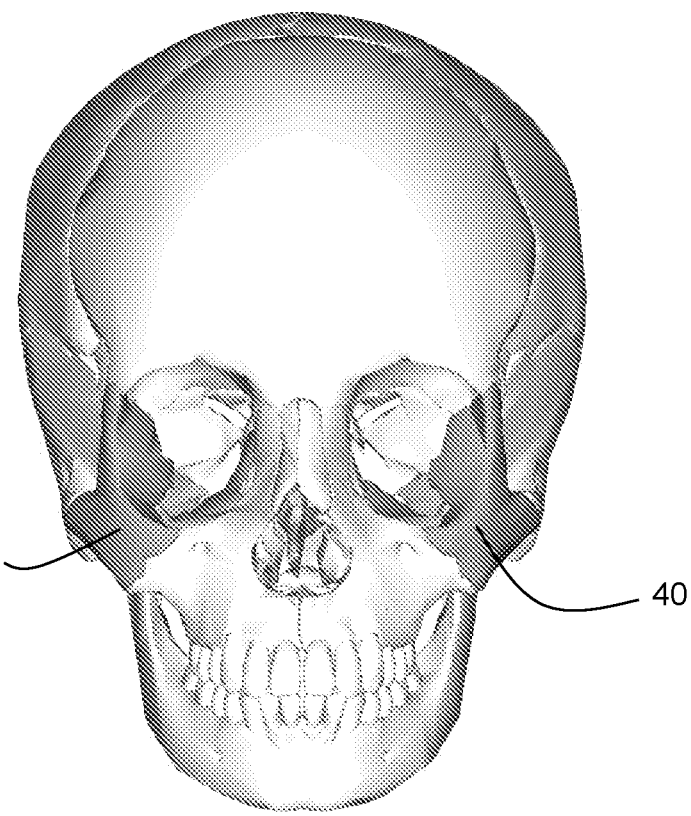
Fig. 3a
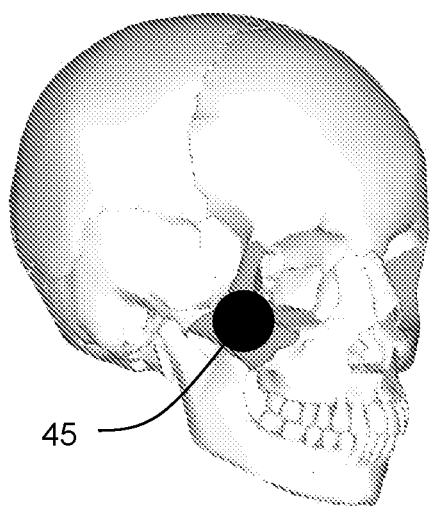 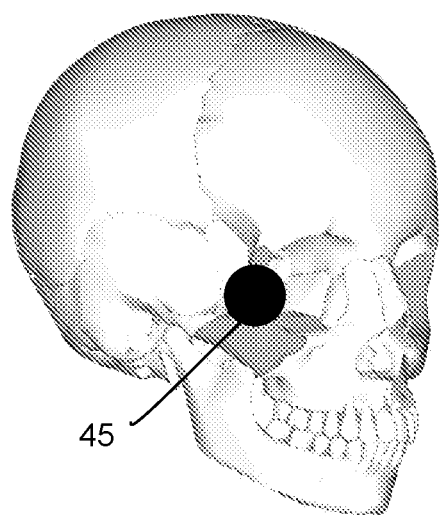
Fig. 3b                Fig. 3c

SYSTEM AND METHOD OF TREATING PAIN WITH EXTERNAL TRANS-ZYGOMATIC ARCH PHOTIC STIMULATION

CROSS-REFERENCE TO RELATED APPLICATIONS

This application claims priority to U.S. Provisional Patent Application No. 63/238,843, filed Aug. 31, 2021 and to U.S. Provisional Patent Application No. 63/217,481, filed Jul. 1, 2021, the entire contents of both are incorporated by reference herein.

TECHNICAL FIELD

The presently disclosed subject matter is generally directed to a system and method of treating and/or preventing acute and chronic pain (e.g., migraine headaches, dental pain). Specifically, the disclosed system and method includes the use of external trans-zygomatic arch photic stimulation to modulate trigeminal ganglion circuits expressing calcitonin gene-related peptide and other inflammatory mediators of migraine headaches, dental pain, and the like.

BACKGROUND

Painful conditions of the head are well known. For example, migraine headaches are one of the most common conditions associated with central nervous system nerve transmission and dysfunction. central. According to the American Migraine Foundation, migraines affect approximately 12% of the U.S. population (2021). Further, in the Global Burden of Disease Study by the World Health Organization (updated in 2013) migraine was found to be the sixth highest cause worldwide of years lost due to disability. Historically, prevention of migraine utilizes medications such as antidepressants, anticonvulsants, antihypertensives, and the pharmaceutical treatment of migraine has been extensively investigated. In addition, conventional treatment options for ongoing symptomatic pain associated with migraine headaches include non-opiate and opiate class pharmaceuticals, caffeine, and anti-inflammatory drugs. Due to the side effects associated with pharmaceutical treatments of migraine and their limited effectiveness, other conventional ways of the treatment of migraine and other types of cranial and head pain and dysfunction arising from disturbances of neuronal function have been developed. For example, acupuncture, biofeedback treatment, and chiropractic adjustment Internal stimulation or block of the sphenopalatine ganglia, sphenopalatine nerve, or vidian nerve have been studied by passing a cotton pledget with lidocaine, or laser illumination internally through the open nostril to the sphenopalatine ganglion, have been contemplated in prior art. However, the internal approaches are expensive to perform, invasive, are expensive, time consuming, and/or produce limited results with risk of local injury and discomfort.

Further, most people dread going to the dentist and equate such visits with pain. The most severe pain is typically caused by the drilling of cavities, root canal procedures, the pulling of teeth, crown and bridge work, and other procedures that disrupt, damage, or otherwise put pressure on the pulp of a tooth and/or the surrounding maxillary bone and gingiva. Various techniques are commonly used to reduce the pain associated with dental procedures. For example, the application of a local anesthetic into the surrounding gingival tissue adjacent to the tooth is frequently used to reduce or eliminate pain. However, the application of a local anesthetic by needle injection is very painful. In addition, the fear of needles is so great in some individuals that the injection can be more traumatic than the dental procedure itself. In addition, local anesthesia can be incorrectly placed, resulting in failure of the anesthesia. The proper dosage of anesthesia can also vary greatly from one patient to the next and due to biological variation, anxiety, fear, or infection in the area. Further, complications such as infections, damage to local tissue/nerves, and laceration of blood vessels can also occur with local injections.

It would therefore be beneficial to provide a system and method of reducing or eliminating migraine headaches, dental pain associated with a procedure (e.g., removal of teeth) or condition (e.g., cavity), and other associated conditions that overcomes the shortcomings of the prior art by utilizing an external approach.

SUMMARY

In some embodiments, the presently disclosed subject matter is directed to a method of treating head pain (e.g., migraine, chronic migraine, and/or dental pain) in a patient. Particularly, the method comprises positioning a light source proximal to the skin surface overlying the trigeminal ganglion. The method further includes emitting a wavelength of light with the light source. The method comprises transmitting the wavelength of light from the external location on the skin through the facial tissues to the underlying trigeminal ganglion ("transillumination of the trigeminal ganglion"), the light (e.g., light impulses) being sufficient to stimulate the neuronal cells of the trigeminal ganglion to at least partially relieve the dental pain.

The term "proximal" refers to a location at or near a skin surface. Thus, in some embodiments, the light source can contact the skin surface overlaying the trigeminal ganglion. In other embodiments, the light source does not physically touch the skin, but is positioned in line (e.g., directly above) the trigeminal ganglion on the exterior surface of the patient's body.

In some embodiments, the presently disclosed subject matter is directed to a method of preventing dental pain in a patient. The method comprises positioning a light source proximal to the skin surface overlying the trigeminal ganglion on one or both sides of the patient's head. The method also includes emitting a wavelength of light with the light source and transmitting the wavelength of light to the trigeminal ganglion, the light impulses being sufficient to stimulate the neuronal cells of the trigeminal ganglion to prevent the dental pain from occurring.

In some embodiments, the positioning comprises placing the light source on the zygomatic arch on one or both sides of the patient's head.

In some embodiments, the light source is configured to generate light with a wavelength of about 300-1200 nanometers.

In some embodiments, the light source is a laser.

In some embodiments, the laser is selected from an Ar laser, He—Ne laser, Ga—Al—As laser, or combinations thereof.

In some embodiments, the light source is a light emitting diode.

In some embodiments, the generating comprises pulsing in a manner that quenches or kindles neurons of the trigeminal ganglion.

In some embodiments, the light source is worn by the patient.

In some embodiments, the patient is a human.

In some embodiments, a controller is configured to regulate an output of the light source based on the EMF (electromagnetic field) collected within MRI low field operative suite for simultaneous imaging and treatment.

In some embodiments, a controller is configured to regulate an evoked response of the patient, trigeminal nerve evoked response, EKG, GSR, sleep stage recorder, or an electroencephalogram.

In some embodiments, the method is sufficient to at least partially relieve the dental pain within 1 minute of the transmitting step.

In some embodiments, the dental pain is a symptom of one or more of dental cavities, tooth decay, acute injury, dental infection, gum disease, plaque, dental decay, cracked teeth, newly placed or adjusted fittings or crowns, poorly placed fittings or crowns, failing crowns or fillings, dental fillings, loss of a tooth, extractions, temporomandibular joint (TMJ) disorders, obstructive sleep apnea, teeth grinding, teeth clenching, gingivitis, periodontal disease, acid erosion, tooth fracture, damaged/broken fillings, damaged/broken crowns, cold sores, canker sores, gum recession, impacted wisdom tooth, abscessed tooth, orthodontic movement, root canals, placement of dental implants, gum tissue grafts, and dental x-rays.

In some embodiments, the presently disclosed subject matter is directed to a device for positioning a light source adjacent to skin surface of the trigeminal ganglion in a patient, the device comprising a light source configured proximally to the skin surface of the trigeminal ganglion on one or both sides of the head when worn. In some embodiments, the device is configured for use in treating dental pain.

In some embodiments, the device comprises a controller configured to control operation of the light source.

In some embodiments, the generating comprises pulsing in a manner that quenches or kindles neurons of the trigeminal ganglion.

In some embodiments, the presently disclosed subject matter is directed to a method of treating dental pain in a patient. Particularly, the method comprises positioning a light source proximal to the skin surface overlying the trigeminal ganglion. The method further includes emitting a wavelength of light with the light source. The method comprises transmitting the wavelength of light from the external location on the skin through the facial tissues to the underlying trigeminal ganglion ("transillumination of the trigeminal ganglion"), the light impulses being sufficient to stimulate the neuronal cells of the trigeminal ganglion to at least partially relieve the dental pain.

In some embodiments, the presently disclosed subject matter is directed to a method of preventing dental pain in a patient. The method comprises positioning a light source proximal to the skin surface overlying the trigeminal ganglion on one or both sides of the patient's head. The method also includes emitting a wavelength of light with the light source and transmitting the wavelength of light to the trigeminal ganglion, the light impulses being sufficient to stimulate the neuronal cells of the trigeminal ganglion to prevent the dental pain from occurring.

In some embodiments, the positioning comprises placing the light source on the zygomatic arch on one or both sides of the patient's head.

In some embodiments, the light source is configured to generate light with a wavelength of about 300-1200 nanometers.

In some embodiments, the light source is a laser.

In some embodiments, the laser is selected from an Ar laser, He—Ne laser, Ga—Al—As laser, or combinations thereof.

In some embodiments, the light source is a light emitting diode.

In some embodiments, the generating comprises pulsing in a manner that quenches or kindles neurons of the trigeminal ganglion.

In some embodiments, the light source is worn by the patient.

In some embodiments, the patient is a human.

In some embodiments, a controller is configured to regulate an output of the light source based on the EMF collected within MRI low field operative suite for simultaneous imaging and treatment.

In some embodiments, a controller is configured to regulate an evoked response of the patient, trigeminal nerve evoked response, EKG, GSR, sleep stage recorder, or an electroencephalogram.

In some embodiments, the method is sufficient to at least partially relieve the dental pain within 1 minute of the transmitting step.

In some embodiments, the dental pain is a symptom of one or more of dental cavities, tooth decay, acute injury, dental infection, gum disease, plaque, dental decay, cracked teeth, newly placed or adjusted fittings or crowns, poorly placed fittings or crowns, failing crowns or fillings, dental fillings, loss of a tooth, extractions, temporomandibular joint (TMJ) disorders, obstructive sleep apnea, teeth grinding, teeth clenching, gingivitis, periodontal disease, acid erosion, tooth fracture, damaged/broken fillings, damaged/broken crowns, cold sores, canker sores, gum recession, impacted wisdom tooth, abscessed tooth, orthodontic movement, root canals, placement of dental implants, gum tissue grafts, and dental x-rays.

In some embodiments, the presently disclosed subject matter is directed to a device for positioning a light source adjacent to skin surface of the trigeminal ganglion in a patient, the device comprising a light source configured proximally to the skin surface of the trigeminal ganglion on one or both sides of the head when worn. In some embodiments, the device is configured for use in treating dental pain.

In some embodiments, the device comprises a controller configured to control operation of the light source.

In some embodiments, the generating comprises pulsing in a manner that quenches or kindles neurons of the trigeminal ganglion.

In some embodiments, the presently disclosed subject matter is directed to a method of preventing head pain in a patient. Specifically, the method comprises positioning a light source proximal to the skin surface overlying the trigeminal ganglion. The method includes emitting a wavelength of light with the light source and transmitting the wavelength of light to the trigeminal ganglion, the light impulses being sufficient to stimulate the neuronal cells of the trigeminal ganglion to prevent the head pain from occurring.

In some embodiments, the presently disclosed subject matter is directed to a device for positioning a light source adjacent to skin surface of the trigeminal ganglion in a patient. Particularly, the device comprises a light source configured proximally to the skin surface of the trigeminal ganglion when worn. The light source is configured to generate light in a pulsing pattern with a wavelength of about 300-1200 nanometers, and the light source is selected from an Ar laser, He—Ne laser, Ga—Al—As laser, or combinations thereof. In some embodiments, the light source is positioned proximal to the skin surface of the trigeminal ganglion on both sides of the patient's head.

BRIEF DESCRIPTION OF THE DRAWINGS

FIG. 3a is a front plan view of a zygotic arch in a human skull.

FIGS. 3b-3d are perspective views of the zygotic arch in a human skull, relative to placement of a light source in accordance with some embodiments of the presently disclosed subject matter.

DETAILED DESCRIPTION

Figure 1:
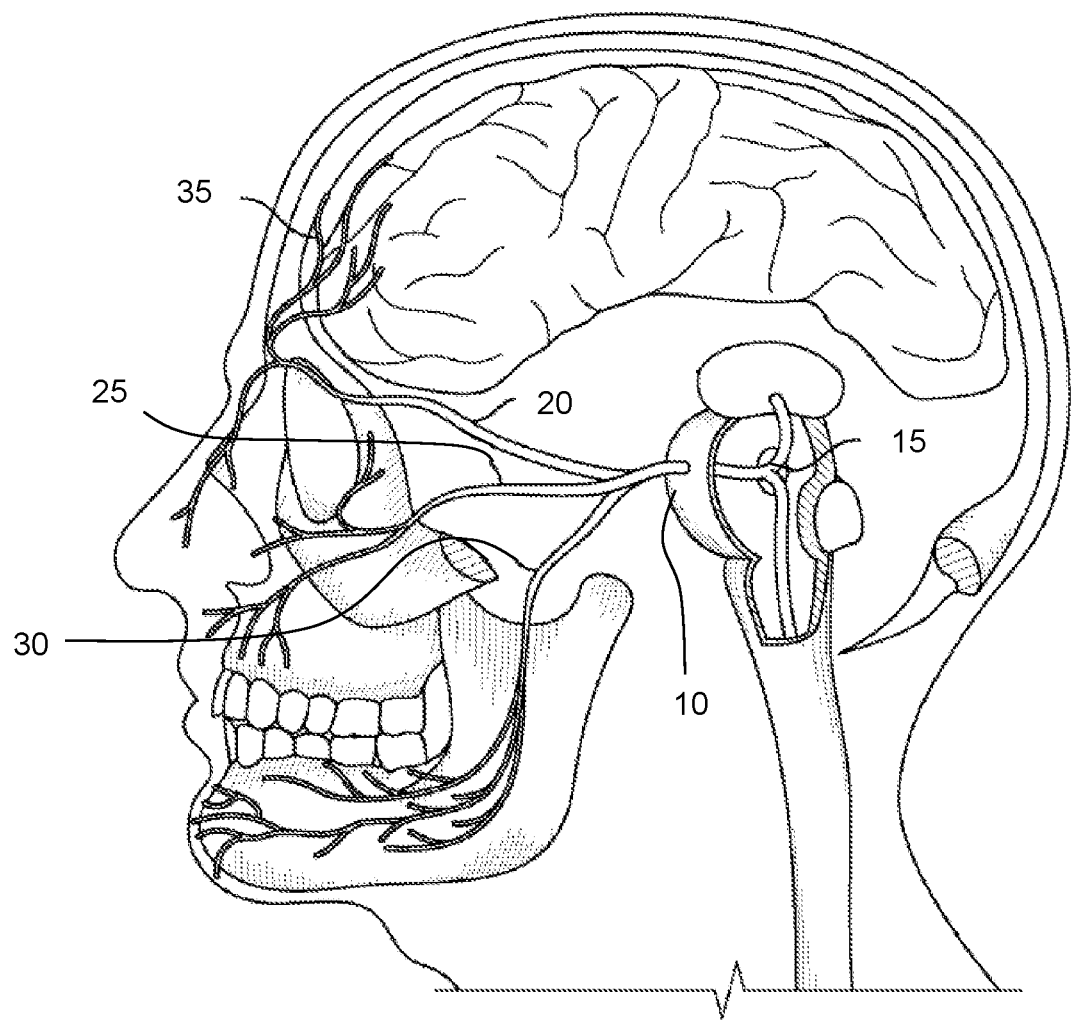
FIG. 1 is a cross-sectional view illustrating the trigeminal nerve in a human skull.

The presently disclosed subject matter is introduced with sufficient details to provide an understanding of one or more particular embodiments of broader inventive subject matters. The descriptions expound upon and exemplify features of those embodiments without limiting the inventive subject matters to the explicitly described embodiments and features. Considerations in view of these descriptions will likely give rise to additional and similar embodiments and features without departing from the scope of the presently disclosed subject matter.

Unless defined otherwise, all technical and scientific terms used herein have the same meaning as commonly understood to one of ordinary skill in the art to which the presently disclosed subject matter pertains. Although any methods, devices, and materials similar or equivalent to those described herein can be used in the practice or testing of the presently disclosed subject matter, representative methods, devices, and materials are now described.

Following long-standing patent law convention, the terms "a", "an", and "the" refer to "one or more" when used in the subject specification, including the claims. Thus, for example, reference to "a device" can include a plurality of such devices, and so forth. It will be further understood that the terms "comprises," "comprising," "includes," and/or "including" when used herein specify the presence of stated features, integers, steps, operations, elements, and/or components, but do not preclude the presence or addition of one or more other features, integers, steps, operations, elements, components, and/or groups thereof.

Unless otherwise indicated, all numbers expressing quantities of components, conditions, and so forth used in the specification and claims are to be understood as being modified in all instances by the term "about". Accordingly, unless indicated to the contrary, the numerical parameters set forth in the instant specification and attached claims are approximations that can vary depending upon the desired properties sought to be obtained by the presently disclosed subject matter.

As used herein, the term "about", when referring to a value or to an amount of mass, weight, time, volume, concentration, and/or percentage can encompass variations of, in some embodiments +/−20%, in some embodiments +/−10%, in some embodiments +/−5%, in some embodiments +/−1%, in some embodiments +/−0.5%, and in some embodiments +/−0.1%, from the specified amount, as such variations are appropriate in the disclosed packages and methods.

As used herein, the term "and/or" includes any and all combinations of one or more of the associated listed items.

Relative terms such as "below" or "above" or "upper" or "lower" or "horizontal" or "vertical" may be used herein to describe a relationship of one element, layer, or region to another element, layer, or region as illustrated in the drawing figures. It will be understood that these terms and those discussed above are intended to encompass different orientations of the device in addition to the orientation depicted in the drawing figures.

The embodiments set forth below represent the necessary information to enable those skilled in the art to practice the embodiments and illustrate the best mode of practicing the embodiments. Upon reading the following description in light of the accompanying drawing figures, those skilled in the art will understand the concepts of the disclosure and will recognize applications of these concepts not particularly addressed herein. It should be understood that these concepts and applications fall within the scope of the disclosure and the accompanying claims.

The presently disclosed subject matter is directed to the use of an external photic stimulator to treat and/or prevent pain, such as pain in the head (e.g., migraine headaches, dental pain, and the like). The term "treating pain" refers to a method of providing a subject with certain relief (e.g., about 50% relief, 75% relief, 100% relief compared to a control) from one, a few, or all pain symptoms. The term "preventing pain" refers to reducing, delaying, or eliminating the sensation of pain before, during, or after the pain occurs. "Head pain" can refer to the sensation of pain the head, including pain from migraine headache, chronic migraine headache, dental pain, tension headaches, analgesic rebound headaches, episodic cluster headaches, chronic cluster headaches, cluster variants, chronic paroxysmal hemicrania, hemicrania continua, post-traumatic headache, post-traumatic neck pain, post-herpetic neuralgia involving the head or face, pain from spine fracture secondary to osteoporosis, arthritis pain in the spine, headache related to cerebrovascular disease and stroke, headache due to vascular disorder, reflex sympathetic dystrophy, cervicalgia (which may be due to various causes, including, but not limited to, muscular, discogenic, or degenerative, including arthritic, posturally related, or metastatic), glossodynia, carotidynia, cricoidynia; otalgia due to middle ear lesion, maxillary neuralgia, laryngeal pain, myalgia of neck muscles, trigeminal neuralgia (sometimes also termed tic douloureux), post-lumbar puncture headache, low cerebro-spinal fluid pressure headache, temporomandibular joint disorder, atypical facial pain, ciliary neuralgia, paratrigeminal neuralgia (sometimes also termed Raeder's syndrome), petrosal neuralgia, Eagle's syndrome, idiopathic intracranial hypertension, orofacial pain, myofascial pain syndrome involving the head, neck, and shoulder; chronic migraneous neuralgia, cervical headache, paratrigeminal paralysis, sphenopalatine ganglion neuralgia (sometimes also termed lower-half headache, lower facial neuralgia syndrome, Sluder's neuralgia, and Sluder's syndrome), carotidynia, Vidian neuralgia, and causalgia, or a combination of the above. In some embodiments, the head pain can include dental pain, dental cavities, tooth decay, acute injury, dental infection, gum disease, plaque, dental decay, cracked teeth, newly placed or adjusted fittings or crowns, poorly placed fittings or crowns, failing crowns or fillings, dental fillings, loss of a tooth, extractions, temporomandibular joint (TMJ) disorders, obstructive sleep apnea, teeth grinding, teeth clenching, gingivitis, periodontal disease, acid erosion, tooth fracture, damaged/broken fillings, damaged/broken crowns, cold sores, canker sores, gum recession, impacted wisdom tooth, abscessed tooth, orthodontic movement, root canals, placement of dental implants, gum tissue grafts, and dental x-rays.

As shown in FIG. 1, the trigeminal nerve emerges from the brainstem on the midlateral surface of pons 10 as a large sensory root and a smaller motor root. The sensory ganglion (trigeminal ganglion) 15 sits in a depression or the trigeminal cave, also known as Meckle's cave. The trigeminal ganglion is analogous to the dorsal root ganglia of the spinal cord, which contain the cell bodies of incoming sensory fibers from the rest of the body. From the trigeminal ganglion 15, ophthalmic branch (V1) nerve 20 exits the skull via the superior orbital fissure, maxillary branch 25 exits via the foramen rotundum and mandibular branch (V3) 30 exits via the foramen ovale. As the nerves exit the skull or cranial cavity, each nerve branches extensively into peripheral branches 35.

Prior art photic treatment of migraine headaches has included the use of needles or inserted pledges positioned within the patient's nasal cavity. However, these methods are painful for the patient, and are difficult to perform due to nasal passage variances, variability in sensitivity to local anesthetics, and the length of time for a local anesthetic to take effect by diffusion from a cotton pledget (up to 45 minutes in the recumbent position) 45 minutes). The presently disclosed method is an improvement over the prior art methods and includes treating migraine headaches externally through the cheek, over the zygomatic arch and area of the trigeminal ganglion. Without being bound by any particular theory, external photic stimulation is believed to modulate the trigeminal ganglion circuits, preventing the expression of calcitonin gene-related peptides and other inflammatory manifestations of migraine headache and inducing an inhibitory wave which induces release of inhibitory substances that normalize the hyperfunctioning ganglion. Thus, in essence the disclosed system and method induces a temporary "nap" for the specific nerves in the migraine pain circuit, immediately interrupting overactive inflammatory and pain processes and providing time for reintegration with other circuits and healing.

Similarly, prior art treatment of dental pain has included the use of needles to inject local anesthetic into the oral tissues. However, these methods are painful for the patient, and are difficult to perform due to precise location of nerves, variability in sensitivity to local anesthetics, and the length of time for a local anesthetic to take effect. Topical anesthetics in the form of gels, liquids, sprays, or patches to the gingival area are also commonly used. However, topical anesthetics are only effective at relieving pain associated with superficial procedures, such as suturing a laceration. Thus, topical anesthetics do not effectively alleviate dental pain involving a tooth or the surrounding bone. The presently disclosed method is an improvement over the prior art methods and includes treating dental pain externally through the cheek, over the zygomatic arch and area of the trigeminal ganglion. Without being bound by any particular theory, external photic stimulation is believed to modulate the trigeminal ganglion circuits, preventing the expression of inflammatory manifestations associated with dental pain. Thus, in essence the disclosed system and method induces a temporary "nap" for the specific nerves in the dental pain circuit, immediately interrupting overactive inflammatory and pain processes and providing time for reintegration with other circuits and healing.

The term "migraine headache" as used herein refer to x. The term "chronic migraine" refers to x. The term "dental pain" refers to x.

Figure 2:
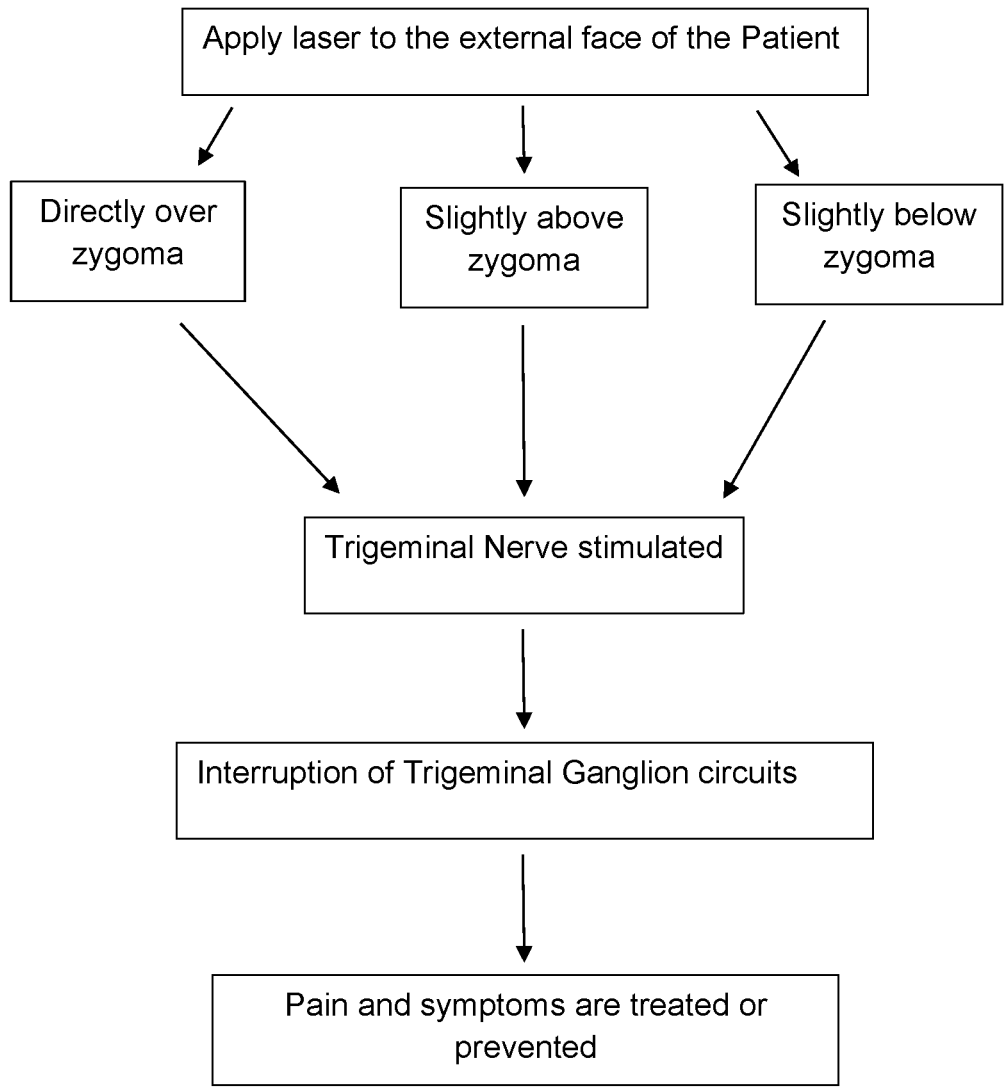
FIG. 2 is a schematic illustrating one method of treating or preventing migraine headache in a subject in accordance with some embodiments of the presently disclosed subject matter.
Figure 3D:
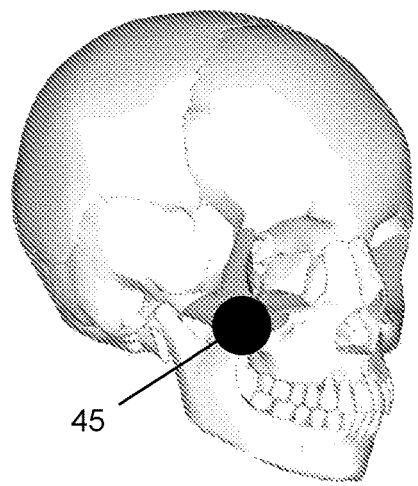

FIG. 2 is a schematic illustrating one method of treating a patient in need thereof (e.g., a patient exhibiting pain symptoms). As shown, a light source is applied to the external face of the patient on the side of the pain at or around the zygoma. The term "zygoma" generally refers to the zygomatic bone, commonly referred to as the zygomatic arch. FIG. 3a illustrates the location of zygoma 40 on either side of a patient skull. In some embodiments, the laser can be applied at location 45 directly over the zygoma, slightly above the zygoma, and/or slightly below the zygoma, as illustrated in FIGS. 3b-3d, respectively. The term "slightly" can refer to an offset of about 1-25 percent in some embodiments. In some embodiments, the light source can be angled towards the trigeminal ganglion to provide maximum transillumination, which is evidenced by the maximum transillumination diameter around the point of application. The light source is typically applied to the side of the head that is experiencing the migraine pain, although either side (or both sides) can be treated.

The term "laser" refers to any device that emits light through a process of optical amplification (e.g., based on the stimulated emission of electromagnetic radiation). Suitable lasers can include (but are not limited to) an Ar laser, He—Ne laser, Ga—Al—As laser, or combinations thereof. Ar lasers utilize argon gas as its lasting medium and produces a visible blue-green beam with wavelengths of about 488 nm and 514 nm. The He—Ne laser (helium-neon laser) is a type of gas laser in which a mixture of helium and neon gas is used as a gain medium (e.g., a mixture of 10:1 helium:neon at a total pressure of about 1 torr inside of a small electrical discharge). The Ga—Al—As laser is an aluminum gallium arsenide diode laser with a wavelength that falls into the infrared region, with a wavelength of about 1064 nm.

As the light source is applied to the zygoma, the trigeminal nerve is stimulated, thereby modulating the trigeminal ganglion and trigeminovascular circuits. As a result, the excessive release of inflammatory manifestations of pain (e.g., dental pain) from the trigeminal ganglion and trigeminovascular circuit is prevented. For example, excessive release of calcitonin gene-related peptides and other inflammatory manifestations of migraine headache from the trigeminal ganglion and trigeminovascular circuit is prevented.

As used herein the term "stimulating" refers to causing a neuron or group of neurons such as a ganglion to be affected by either kindling or quenching its firing. In some embodiments, the neuron can either (reduce or stop activity altogether) or kindle (activate or increase in activity). Depending on the condition to be treated, one having ordinary skill in the relevant art will be able to determine if and/or how a particular neuron needs to be stimulated to achieve the desired treatment effect. For example, it is known that either quenching or kindling of neurons in the head, central nervous system, and peripheral ganglia and nerves can suppress or prevent pain, having been well studied as the biphasic response described by Hamblin and the use of this concept in photobiomodulation (Huang, et al., Biphasic Dose Response in Low Level Light Therapy—An Update, *Dose-Response* 9(4): 602-18 (2011); Hamblin, et al., Low-Level Light THerapy: Photoimodulation, (2018), incorporated by reference herein).

As set forth above, a light source is applied at or around the area of the zygoma of a patient in need of treatment. The term "light source" refers to a device configured to produce light within a predetermined therapeutic window that is neither ionizing nor thermocoagulating. In some embodiments, the light source can produce light that is approximately in an infrared range to ultraviolet range (about 300-1200 nm). Thus, the light source can be in the ultraviolet range (300-40 nm), visible light range (400-700 nm) and/or near infrared range (700-1200 nm). However, the presently disclosed subject matter is not limiting, and the disclosed light source can produce electromagnetic radiation with frequencies outside the ranges given herein.

Figure 4:
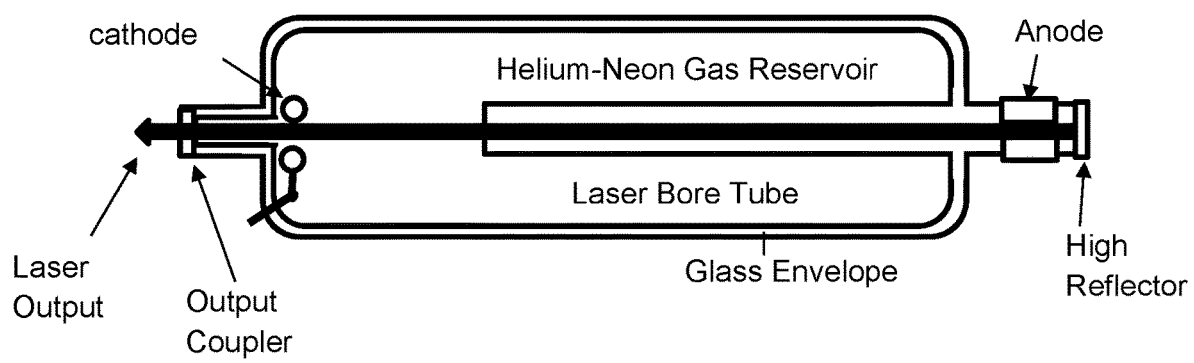
FIG. 4 is a light source in the form of a He—Ne laser in accordance with some embodiments of the presently disclosed subject matter.

The light source can include any type of laser operating within a predetermined range of wavelengths, an LED light source, or any other type of light source suitable for performing stimulation of the neuronal activity. For example, the light source can be a Helium-Neon ("He—Ne") laser configured to emit light at a wavelength of about 600-650 nm (e.g., 632.8 nm). He—Ne lasers typically include a mixture of 10:1 helium:neon and are configured at low pressure in a glass envelope, as shown in FIG. 4. When the gas mixture is stimulated electrically, the helium atoms are excited and collide with the neon atoms, producing a beam of light in the visible spectrum.

The light source can also include Argon ("Ar") lasers that operate at approximately 488 nm and can optionally be outfitted with fiber optic extensions. Further examples include Gallium Arsenide ("Ga—As") and Gallium Aluminum Arsenide ("Ga—Al—As") laser, which are types of semiconductor lasers that emit a wavelength in the 850 nm range or near infrared band of the spectrum. In these lasers, the diode can be operated through a low powered electronic circuit utilizing internal optical feedback to maintain a constant power output.

In some embodiments, the light source can include a light emitting diode (LED). LEDs are semiconductor light sources that emit light when current flows through it. Specifically, electrons in the semiconductor recombine with electron holes, releasing energy in the form of photons. The color of the light (corresponding to the energy of the photons) is determined by the energy required for electrons to cross the band gap of the semiconductor. Thus, LEDs operate in a number of visible wavelengths, are relatively low power, and do not generate large amounts of excess thermal energy. In addition, LEDs can be used with a fiber optic head or extension so that the light source can be narrowly focused.

In some embodiments, the light source includes a controller configured to regulate stimulation of the neuronal activity. The controller can include a central processing unit, a memory, a monitor, a keyboard, a mouse, and/or any other component configured to perform various functions of the controller.

In some embodiments, the controller can be configured to regulate an output of the light source based on a computer-generated algorithm. The computer-generated algorithm can include a predetermined algorithm, or an algorithm based on biofeedback information from at least one biological sensor measuring at least one characteristic of the patient. In some embodiments, the sensor can be placed directly or indirectly on the patient and can measure patient's blood pressure, heart rate, neural response, and/or any other patient-related characteristic.

In some embodiments, the controller can be configured to control output of the light source based on evoked responses of the patient or an electroencephalogram ("EEG"). In some embodiments, the evoked responses are the changes in the trigeminal nerve evoked potential. The EEG can be obtained using at least one scalp electrode coupled to the patient that records at least one characteristic of the patient. The EEG can be analyzed by the controller (e.g., averaging the data received from the EEG to produce a somatosensory evoked potential to determine when a sphenopalatine ganglion block has been completed).

In some embodiments galvanic skin response (GSR), pulse rate, pulse rate variability, temperature, information from the sleep-wake cycle or stages of sleep, or any other biological signal may be utilized to control the output of the light source.

In some embodiments, the controller can automatically stop the stimulation of the neural cell when a specified value of a biological observable variable is reached. Alternatively, when the sphenopalatine ganglion block is completed, the controller can request input from a user (e.g., patient, doctor, nurse).

Using the obtained EEG, EKG, GSR, or other biosensor the controller can also monitor stimulation of neurons of a vagus nerve in the neck of the patient to prevent epileptic seizures. In these embodiments, the controller can generate a stimulus upon detection of epileptic discharges. Similarly, the controller can be configured to monitor blood pressure and/or regulate the stimulation to control blood pressure.

In some embodiments, a coherent laser light can be focused by lenses into a glass-optic assembly attached via a connector to the laser source for convenience and interchangeability. Use of a fiber-optic structure (or other similar extension) allows application of the laser light at a desired location proximate to the neuronal cell such that it is easily maneuverable inside an MRI scanner. It is contemplated that such a fiberoptic extension assembly will be utilized in interventional low field fMRI operating suites to treat migraine within the fMRI scanner and simultaneously monitor progression of treatment.

Figure 5A:
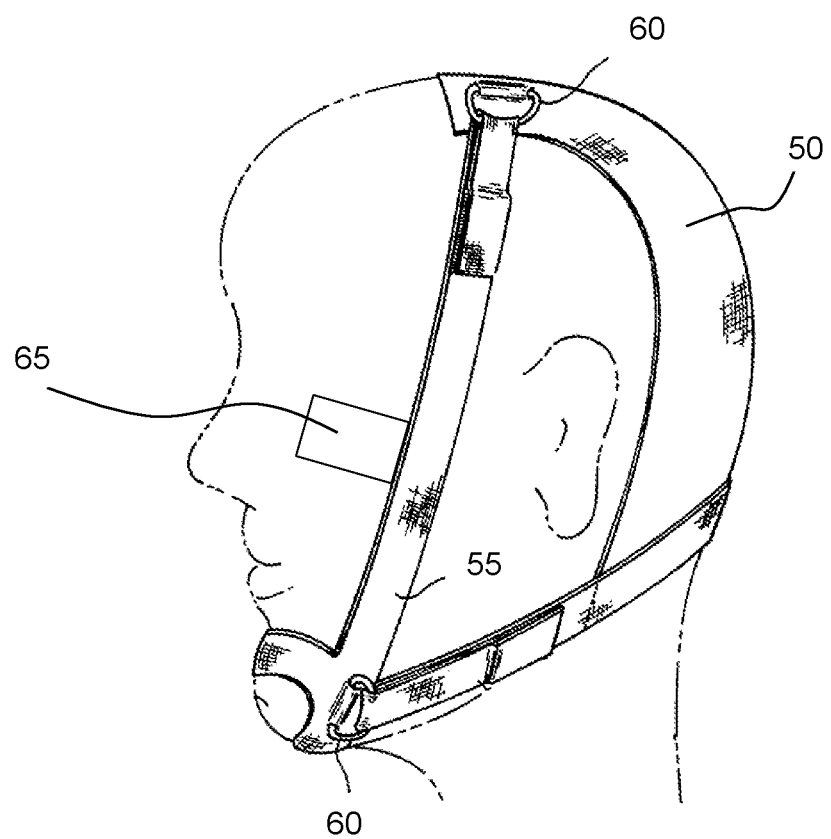
FIG. 5a is a side plan view of a mask comprising a light source in accordance with some embodiments of the presently disclosed subject matter.
Figure 5B:
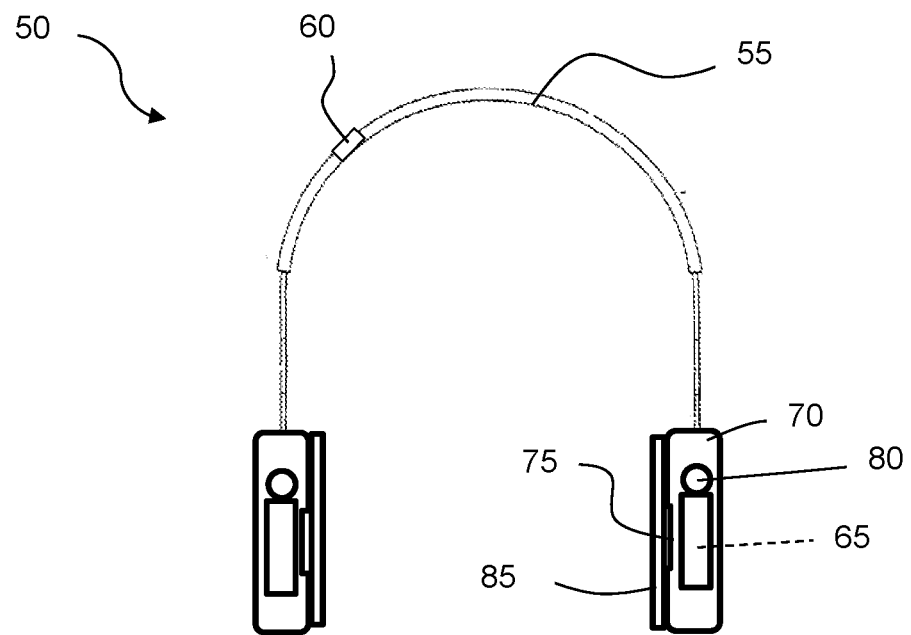
FIG. 5b is a front plan view of a device comprising a light source in accordance with some embodiments of the presently disclosed subject matter.
Figure 5C:
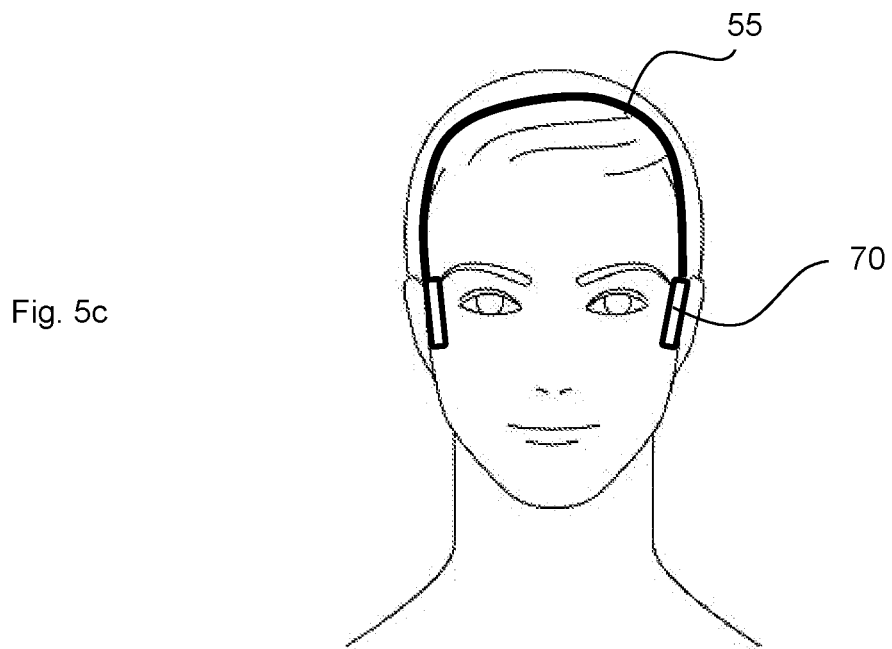
FIG. 5c is a front plan view of a device comprising a light source in use on a patient in accordance with some embodiments of the presently disclosed subject matter.
Figure 5D:
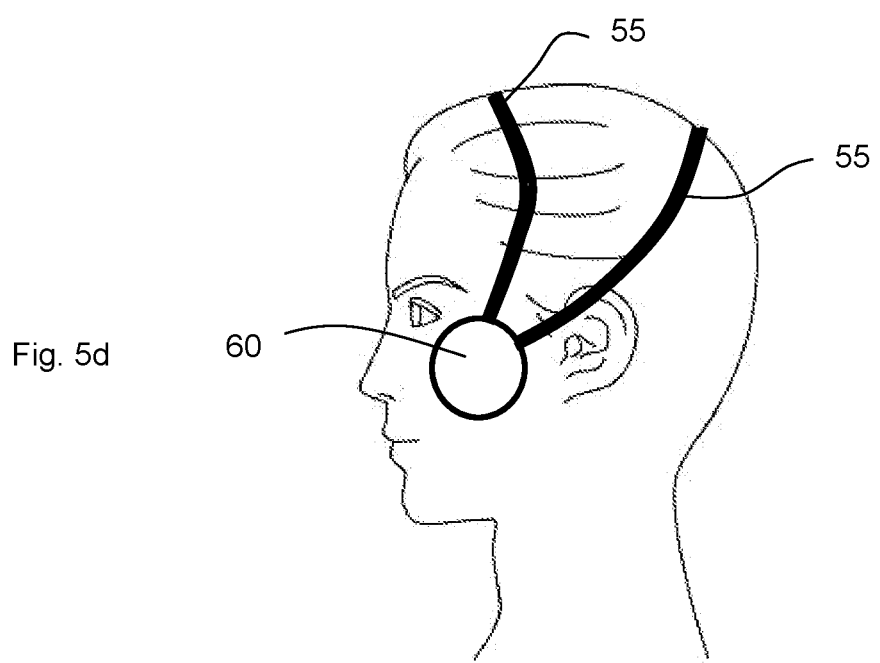
FIG. 5d is a side plan view of a device comprising a light source in use on a patient in accordance with some embodiments of the presently disclosed subject matter.

In some embodiments, the light source can be configured as a bilateral device that is worn by the patient. The term "device" refers to a covering for all or part of the face of a patient. FIGS. 5*a*, 5*c*, and 5*d* illustrate one representative version of device 50 configured to be attached to the head of a patient. As shown, the device can include any of a wide variety of straps 55, buckles 60 and the like to allow the device to be adjusted and retained on the face of a patient. The device also includes light source 65 that is positioned at or near the zygomatic arch and area of the trigeminal ganglion. The light source can be positioned within housing 70 constructed from any of a wide variety of materials that are impermeable to the light source to prevent inadvertent or accidental exposure, as shown in FIG. 5*b*. Each housing includes an aperture or window 75 configured to allow internal light source 65 to be directed at the zygoma on either (or both) side of the patient's head. The housing can further include one or more power sources (e.g., batteries 80) for light source 65.

In some embodiments the device can include disposable contact 85 that provides a sanitation function. The contact acts as an interface between the light source and window and the skin of the patient. The contact can be any material that does not filter or obstruct the light source. Thus, the contact can be constructed from any transparent material, such as clear plastic. After use, the contact can be removed, and a new contact added prior to use with a subsequent patient.

The device can include optional optical shields that protect the patient's eyes from exposure to light source 65. The optical shields can include any element that fully or partially screens the user's eyes, such as the use of goggles, guards, and the like.

It should be appreciated that device 50 is not limited to any particular design so long as it includes light source 65 configured to be positioned at or near the patient's trigeminal ganglion on one or both sides of his/her face.

In use, straps and buckles 55, 60 can be positioned on any portion of the user's head to secure placement of the housing (and light source 65) over the patient zygoma. For example, at least one strap can be positioned at the top portion of the user's head (e.g., similar to headphones), as shown in FIGS. 5b and 5c. In some embodiments, the device can include at least one strap configured to be worn around the chin, as shown in FIG. 5d. Any suitable configuration of the adjustment around the user's head can be used.

Device 50 can be controlled using a simple on/off switch. Alternatively, the device can be controlled remotely, such as through a computer, smart phone, or other element. For example, the device can be activated such that a single light source is initiated on one side of the user's head (e.g., the side of the head with dental pain). In some embodiments, the light source of both sides of the device can be activated simultaneously. Each light source can be independently controlled relative to the other light source. Thus, a first light source can be positioned at a first frequency that is greater than, less than, or about the same as the second light source positioned on the opposite side of the patient's face. Similarly, the first light source can be activated for a time that is greater than, less than, or about equal to the second light source.

The light produced by light source 65 can be pulsed or configured as a continuous wave. As used herein the term "pulsed" refers to the turning on and off (in the form of a cycle) at a predetermined rate. For example, if the light is pulsed at a slow rate, the neuron may be allowed to recover before the next stimulation pulse and then it is kindled. In some embodiments, if the frequency of pulses less than 400 msec, it is sufficient to kindle neurons in the head. However, if the frequency of the light pulse is greater than the recovery time of the cell, (about 400 msec in mammals) the activity of the cell can be at least partially quenched.

In addition to the direct effect of kindling or quenching the nerve being stimulated, higher order effects on other reverberating circuits are present which may affect other biological characteristics such as mood and sleep. As can be understood by one having ordinary skill in the relevant art, pulse rates to achieve a desired stimulation effect (such as immediate reduction in anxiety) can be readily determined. for the individual patient and their current state of anxiety or alertness. Pulsing as the alpha frequency of around 8-12 cps for 30-60 seconds at any site over the cranium, including over the trigeminal ganglion, often induces a sense of relaxation which may contribute to overall comfort and a more complete response.

In some embodiments, the light source stimulation can be modulated to prevent occurrence of unwanted disruption of intracranial connections ("Connectome") which may be imaged by fMRI. the fMRI connectome studies may be performed prior to and after treatment for monitoring and modulating higher effects on the connectome or may be obtained in a low field fMRI operative suite for simultaneously guiding interventional therapy.

In some embodiments, a single treatment can be applied to a patient during a predetermined period of time, such as prior to menses, prior to a dental procedure, just prior to a migraine triggering event, etc. In alternate embodiments, multiple treatments each having a predetermined application time can be applied, where a total application time of all treatments can be predetermined.

It should be appreciated that the amount of time that the light source is used to stimulate a neuron can vary based on the severity of the pain (e.g., migraine), patient age, patient gender, menstrual cycle, patient weight, wavelength of light source, type of laser, and/or the like. For example, treatments can be about 5 seconds to 10 minutes in length but are typically 30 to 60 seconds. Treatments can be repeated as needed depending, for example, on the severity and type of disorder being treated, the type of light, and/or light source's exact positioning in the patient.

The term "patient" broadly refers to any subject in need of treatment. Thus, the patient can be a human patient exhibiting pain or that is believed to be exhibiting pain in the future. The pain can be in the form of a migraine headache. Alternatively, the patient can be a human patient currently experiencing or believed to at some point in the future experience dental pain. However, the patient is not limited and the presently disclosed subject matter can be used with veterinary purposes for the treatment of dogs, cats, goats, horses, ponies, donkeys, rabbits, and the like.

The disclosed methods can be used under the supervision of a medical practitioner (e.g., doctor, nurse, physician's assistant, home health care worker). Alternatively, the disclosed system and method can be used by the patient directly, without supervision. For instance, the medical practitioner can program the device (e.g., mask, light source, etc.) after an initial acute treatment. The patient can then resume treatments as needed or as specified by the medical practitioner. For example, to prevent the onset of a migraine headache, the patient can wear device 50 for 20 minutes, twice daily. In other embodiments, the system can be used to treat a migraine headache, such as exposing the zygoma on the affected side of the head to light source 65 pulses for about 2 minutes. In this way, the presently disclosed subject matter allows for patient chronic self-treatment. It should be appreciated that patient treatment times are not limited to the examples given herein and can vary.

In some embodiments, the acute or long-term treatment can be paired with one or more substances with trophic effects, whether anabolic or catabolic. Such substances can include (but are not limited to) hormones (e.g., dexamethasone, prednisone, liothyronine, anabolic steroids, insulin) and substances active in the electron chain transport (e.g., B vitamins, ubiquinone, methylene blue) administered orally, intranasally, transdermally, and/or intravenously during the course of short or prolonged treatment. Further, in some embodiments, treatment can be paired with immersion in virtual reality environments for enhancement of diagnostic and/or therapeutic effects.

Although described primarily for use in treating and/or preventing the onset of pain (such as migraine headaches and dental pain), the presently disclosed subject matter is not limited. For example, the disclosed system and method can be used for the prevention and/or treatment of snoring. The term "snoring" refers to a pharyngeal vibratory state. For example, snoring can be characterized by sounds emanating from the upper airway of a patient, louder than 60 dB and having a duration between about 0.25 and 5 seconds. A patient can wear mask 50 (or otherwise be exposed to light source 65 over the zygoma on one or both sides of the head. The stimulation can occur day or night for variable times to achieve a total power deposition sufficient to modulate or eliminate the symptoms of snoring.

In addition, the disclosed system and method can be used to treat or prevent TMJD. TMJD is characterized by pain and dysfunction of the muscles of mastication (the muscles that move the jaw) and the temporomandibular joints (the joints that connect the mandible to the skull). A patient can wear mask 50 (or otherwise be exposed to light source 65 over the zygoma on one or both sides of the head. The stimulation can occur day or night for variable times to achieve a total power deposition sufficient to modulate or eliminate the symptoms of TMJ.

Further, the disclosed system and method utilizes light stimulation of the sphenopalatine ganglion for a treatment of a variety of other medical conditions. Specifically, medical conditions that can be treated by the disclosed system and methods include (but are not limited to): pain, dental pain, movement disorders, epilepsy, cerebrovascular diseases, autoimmune diseases, sleep disorders, autonomic disorders, urinary bladder disorders, abnormal metabolic states, disorders of the muscular system, Alzheimer's disease, other forms of dementia, and/or neuropsychiatric disorders.

Pain treatable by the disclosed systems and methods can be caused by conditions including (but not limited to): migraine headaches, including migraine headaches with aura, migraine headaches without aura, menstrual migraines, migraine variants, atypical migraines, complicated migraines, hemiplegic migraines, transformed migraines, and chronic daily migraines; episodic tension headaches; chronic tension headaches; analgesic rebound headaches; episodic cluster headaches; chronic cluster headaches; cluster variants; chronic paroxysmal hemicrania; hemicrania continua; post-traumatic headache; post-traumatic neck pain; post-herpetic neuralgia involving the head or face; pain from spine fracture secondary to osteoporosis; arthritis pain in the spine, headache related to cerebrovascular disease and stroke; headache due to vascular disorder; reflex sympathetic dystrophy, cervicalgia (which may be due to various causes, including, but not limited to, muscular, discogenic, or degenerative, including arthritic, posturally related, or metastatic); glossodynia, carotidynia; cricoidynia; otalgia due to middle ear lesion; gastric pain; sciatica; maxillary neuralgia; laryngeal pain, myalgia of neck muscles; trigeminal neuralgia (sometimes also termed tic douloureux); post-lumbar puncture headache; low cerebro-spinal fluid pressure headache; temporomandibular joint disorder; atypical facial pain; ciliary neuralgia; paratrigeminal neuralgia (sometimes also termed Raeder's syndrome); petrosal neuralgia; Eagle's syndrome; idiopathic intracranial hypertension; orofacial pain; myofascial pain syndrome involving the head, neck, and shoulder; chronic migraneous neuralgia, cervical headache; paratrigeminal paralysis; sphenopalatine ganglion neuralgia (sometimes also termed lower-half headache, lower facial neuralgia syndrome, Sluder's neuralgia, and Sluder's syndrome); carotidynia; Vidian neuralgia; and causalgia; or a combination of the above.

Movement disorders treatable by the disclosed systems and methods can be caused by conditions including (but not limited to): Parkinson's disease; cerebral palsy; dystonia; essential tremor; and hemifacial spasms. Epilepsy treatable by the disclosed method can be generalized or partial. Cerebrovascular disease treatable by the present invention's systems and methods may be caused by conditions including, but not limited to: aneurysms, strokes, and cerebral hemorrhage. Autoimmune diseases treatable by the present invention's systems and methods include, but are not limited to, multiple sclerosis. Sleep disorders treatable by the inventive method may be caused by conditions including, but not limited to: sleep apnea and parasomnias. Autonomic disorders treatable by the present invention's systems and methods may be caused by conditions including, but not limited to: gastrointestinal disorders, including but not limited to gastrointestinal motility disorders, nausea, vomiting, diarrhea, chronic hiccups, gastroesophageal reflux disease, and hypersecretion of gastric acid; autonomic insufficiency; excessive epiphoresis; excessive rhinorrhea; and cardiovascular disorders including but not limited to cardiac dysrythmias and arrythmias, hypertension, and carotid sinus disease. Urinary bladder disorders treatable by the present invention's systems and methods may be caused by conditions including, but not limited to: spastic or flaccid bladder. Abnormal metabolic states treatable by the present invention's systems and methods may be caused by conditions including, but not limited to: diseases and/or functional disorders of the nerves subserving the pituitary gland, and endocrine system. Disorders of the muscular system treatable by the present invention's systems and methods include, but are not limited to, muscular dystrophy and spasms of the upper respiratory tract and face. Neuropsychiatric disorders treatable by the present invention's systems and methods may be caused by conditions including, but not limited to: depression, schizophrenia, bipolar disorder, obsessive-compulsive disorder, anxiety disorders, panic attacks, and/or phobias.

The present invention is configured to act to suppress or prevent the listed conditions by modulating sensory signal transmission through the autonomic, peripheral, or central nervous system, including pain signals, as the signals traverse the SPG, or other central or peripheral nerves or ganglia accessible by external application of photic stimulation. The abnormal regulation of pain pathways, which may be a feature of the conditions listed above, can cause excitation or a loss of inhibition of those pathways, resulting in an increased perception of pain. Direct light stimulation of the SPG (or other autonomic, peripheral, or central nervous system neurons) is configured to block the transmission of pain signals and stimulate inhibitory feedback of the pain pathways passing through the SPG, or other autonomic, peripheral, or central nervous system neurons, reducing or eliminating the pain experienced by the patient. Similarly, stimulation of the SPG, or other autonomic, peripheral, or central nervous system neurons can be configured to block the transmission of signals other than pain which can provoke or aggravate other undesirable sensations or conditions, such as nausea, bladder disorders, sleep disorders or abnormal metabolic states.

Accordingly, the present invention is not limited to the above neuronal structures and other neurons within the head are also contemplated within the scope of the present disclosure using the same technique as for the above neurons. For example, nerves such as supraorbital, nasociliary, zygomatotemporal, occipital, palatine, or ganglia such as the ciliary and otic, as well as the neurons in the carotid bulb, the vagus nerve, the phrenic nerve, the brachial plexus, the stellate ganglion, and dorsal root nerves and ganglia of the spine.

The presently disclosed system and methods provide advantages over prior art treatment methods. For example, the disclosed method exhibits little or no patient discomfort.

The disclosed method is more effective than prior art methods. For example, prior art intranasal insertion methods are hindered by distance from the ganglion and scattering/attenuation of the light beam.

Further, minimal training or knowledge is needed to administer the disclosed method.

The disclosed system and method are demonstrated in this patient series to be more effective than prior art treatment methods presumably because it does not suffer from the problem of internal treatment (light scattering, comfort, higher energy deposition due to closer proximity, proximity to the posterior and inferior portions of the ganglion due to the direct illumination of the ganglion rather than from the inferior surface through the nose).

A further advantage is that CGRP release is modulated only in the distribution where it is pathological, (the region of the migraine pathology) not in other areas (uterus, heart, etc.).

Exemplary embodiments of the methods and components of the presently disclosed subject matter have been described herein. As noted elsewhere, these embodiments have been described for illustrative purposes only, and are not limiting. Other embodiments are possible and are covered by the presently disclosed subject matter. Such embodiments will be apparent to persons skilled in the relevant art(s) based on the teachings contained herein. Thus, the breadth and scope of the present invention should not be limited by any of the above-described exemplary embodiments but should be defined only in accordance with the following claims and their equivalents.

EXAMPLES

The following Examples provide illustrative embodiments. In light of the present disclosure and the general level of skill in the art, those of ordinary skill in the art will appreciate that the following Examples are intended to be exemplary only and that numerous changes, modifications, and alterations can be employed without departing from the scope of the presently disclosed subject matter.

Example 1

Chronic Migraine Patient Selection 100 patients that fulfilled the criteria for chronic migraine were selected. According to the American Migraine Foundation, "chronic migraine" is defined as having 15 or more headache days per month for more than 3 months, with at least 8 of those days meeting the criteria for a migraine.

To meet the criteria for a migraine, the patient must have had 5 or more attacks fulfilling criteria A-C.

A: headache attacks lasting 4-72 hours (untreated or successfully treated).

B: Headache has at least 2 of the following: (1) unilateral location, (2) pulsating quality, (3) moderate/severe pain intensity, (4) aggravation by/causing avoidance of routine physical activity (walking, climbing stairs, etc.).

C: During headache, at least one of the following: (1) nausea and/or vomiting; (2) photophobia and phonophobia (sensitivity to light and sound).

Example 2

Treatment of Patient for Migraine Headache

The patient and the operator both wore goggles as recommended by the FDA for a class 3-B laser. The patient was seated comfortably, upright, or inclined. A 660 nm 200 MW He—Ne laser was applied (via focused probe from Thor Photomedicine, Ltd., Hampstead, Maryland r). The laser probe tips were infrared, although any type of probe tips could be used (e.g., LED clusters, IR single laser probes, IR laser clusters, red single laser probes, and/or red laser clusters) to the external face on the side of pain, directly over, slightly above, or slightly below the zygomatic arch such that transillumination of the sphenopalatine region of the sinus was evident. The beam was angled toward the trigeminal ganglion, either directly through the zygoma, at a 90-degree angle, or slightly above and downward or below and upward, at the angle that provides maximum transillumination. The beam frequency was 20 KHz and was applied for 30 seconds.

The level of pain was immediately assessed on a scale of 0 to 10. The 30 second pulse was administered up to 4 times (120 seconds total) or until pain level was 1 (very little pain) or 0 (no pain). The effect lasted approximately 4 days and preliminary data indicated it to have preventive effects when performed weekly until headaches go into long term remission, typically 3 to 8 treatments.

Of the 100 patients, 85 had complete relief of pain (e.g., the portion of the pain that was within the distribution of the trigeminal nerve) within 30-120 seconds of treatment time, overall under five minutes for the procedure. In the majority of cases there was complete cessation of pain in under 400 msec after onset of the first stimulus.

Of the remaining 15 patients, pain persisted in 10 patients posteriorly in the area of the superior cervical ganglion (SCG) and responded within 30-90 seconds with external treatment (same protocol) of the SCG.

The remaining 5 patients were absolute non-responders. One was diagnosed with hemicrania continua (a persistent unilateral headache when they subsequently responded to indomethacin). The 4 others had cervical dystonia, a painful chronic neurological movement whose pathophysiology resides in the basal ganglia, The response rate for patients fulfilling the criteria for chronic migraine with other or co-morbid conditions excluded (excluding dystonia and hemicrania continua, concurrent significant degenerative cervical spine disease was shown to be 100%. In comparison, the prior art indicated a lower response rate as previously described.

Secondary co-morbid conditions: Of the 100 patients, 20 also exhibited symptoms of snoring and 20 had TMJDn as a co-morbid condition. All reported marked improvement of snoring and TMJD symptoms.

Example 3

Evoked Potential Testing

The test was done by recording the stimulus (laser light source) and calculating the average EEG waves in a patient to see the response. The patient had a normal response before the procedure and when the test was immediately repeated, the trigeminal evoked response was absent. The amplitude became detectable by the fourth day and returned to normal in seven days. It was concluded that a temporary interruption of nociceptive transmission by the trigeminal nerve sensory path to the cortex was produced. Motor and autonomic functions were not clinically altered.

Advantageously, whole body CGRP signaling was not interrupted. CGRP has many normal functions, and its safety in pregnancy is unknown. Many migraine sufferers are female and of reproductive age and are inadvertently exposed to an injectable CGRP during pregnancy as the duration of effect of injectable monoclonal antibodies to CGRP is approximately three months.

Prophetic Example 4

MRI Imaging of the Trigeminal Nuclei

An MRI study of the trigeminovascular system to prior to and post treatment will be studied.

What is claimed is:

1. A method of treating or preventing a head pain in a patient, the method comprising:
    positioning a light source proximal to the skin surface overlying the trigeminal ganglion;
    emitting a wavelength of light with the light source;
    transmitting the wavelength of light from the external location on the skin through the facial tissues to the underlying trigeminal ganglion ("transillumination of the trigeminal ganglion"), the light being sufficient to stimulate the neuronal cells of the trigeminal ganglion to at least partially relieve pain and symptoms associated with the head pain;
    wherein the generating comprises pulsing in a manner that quenches or kindles neurons of the trigeminal ganglion.

2. The method of claim 1, wherein the positioning comprises placing the light source on the zygomatic arch on one or both sides of the patient's head.

3. The method of claim 1, wherein the light source is configured to generate light with a wavelength of about 300-1200 nanometers.

4. The method of claim 1, wherein the light source is a laser selected from an Ar laser, He—Ne laser, Ga—Al—As laser, or combinations thereof.

5. The method of claim 1, wherein the light source is a light emitting diode.

6. The method of claim 1, wherein the light source is worn by the patient.

7. The method of claim 1, wherein the method is sufficient to at least partially relieve pain associated with the head pain within 1 minute of the transmitting step.

8. The method of claim 1, wherein the head pain is a migraine headache, chronic migraine headache, dental pain, or combinations thereof.

9. The method of claim 1, wherein a controller is configured to regulate an output of the light source based on the electromagnetic field collected within MRI low field operative suite for simultaneous imaging and treatment.

10. The method of claim 1, wherein a controller is configured to regulate an evoked response of the patient, trigeminal nerve evoked response, EKG, GSR, sleep stage recorder, or an electroencephalogram.

11. A method of treating a medical condition at least partially arising from functional disturbances of the trigeminal nucleus, trigeminal nerve, and branches, the method comprising:
    positioning a light source proximal to the skin surface of the trigeminal ganglion;
    emitting a wavelength of light with the light source;
    transmitting the wavelength of light to the trigeminal ganglion, the light impulses being sufficient to stimulate the neuronal cells of the trigeminal ganglion to treat the medical condition;
    wherein the generating comprises pulsing in a manner that quenches or kindles neurons of the trigeminal ganglion.

12. The method of claim 11, wherein the positioning comprises placing the light source on the zygomatic arch on one side of the patient's head.

13. The method of claim 11, wherein the light source is configured to generate light with a wavelength of about 300-1200 nanometers.

14. The method of claim 11, wherein the light source is a laser selected from an Ar laser, He—Ne laser, Ga—Al—As laser, or combinations thereof.

15. The method of claim 11, wherein the light source is a light emitting diode.

16. The method of claim 11, wherein the medical condition is TMJD or snoring.

17. A device for positioning a light source adjacent to skin surface of the trigeminal ganglion in a patient, the device comprising a light source configured proximally to the skin surface of the trigeminal ganglion when worn;
    wherein the light source is configured to generate light in a pulsing pattern with a wavelength of about 300-1200 nanometers; and
    wherein the light source is selected from an Ar laser, He—Ne laser, Ga—Al—As laser, or combinations thereof.

18. The device of claim 17, wherein a light source is positioned proximal to the skin surface of the trigeminal ganglion on both sides of the patient's head.

* * * * *